United States Patent
Caceres et al.

(10) Patent No.: US 10,098,349 B2
(45) Date of Patent: Oct. 16, 2018

(54) HERBICIDAL COMPOSITIONS CONTAINING IMAZAPIC, AMINOPYRALID AND OPTIONALLY METSULFURON

(71) Applicant: Dow AgroSciences LLC, Indianapolis, IN (US)

(72) Inventors: Neivaldo Tunes Caceres, Sao Jose Do Rio Preto (BR); Felipe Pecinatto Daltro, Palmas (BR); Robert A. Masters, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/566,818

(22) Filed: Dec. 11, 2014

(65) Prior Publication Data

US 2015/0173358 A1 Jun. 25, 2015

Related U.S. Application Data

(60) Provisional application No. 61/919,046, filed on Dec. 20, 2013.

(51) Int. Cl.
*A01N 43/50* (2006.01)
*A01N 43/40* (2006.01)
*A01N 47/36* (2006.01)

(52) U.S. Cl.
CPC ............ *A01N 43/40* (2013.01); *A01N 43/50* (2013.01)

(58) Field of Classification Search
CPC combination set(s) only.
See application file for complete search history.

(56) References Cited

U.S. PATENT DOCUMENTS

| 2011/0118120 A1* | 5/2011 | Corr ................ A01N 43/40 504/134 |
| 2011/0190133 A1 | 8/2011 | Epp et al. |
| 2011/0312494 A1 | 12/2011 | Mann et al. |
| 2013/0012386 A1 | 1/2013 | Burke et al. |
| 2013/0143741 A1* | 6/2013 | Wright .............. A01N 25/04 504/128 |
| 2013/0310256 A1 | 11/2013 | Yerkes et al. |

FOREIGN PATENT DOCUMENTS

| WO | WO2010105047 A2 | 9/2010 |
| WO | WO2011113061 A2 | 9/2011 |
| WO | PCT/US14/69665 | 3/2015 |

OTHER PUBLICATIONS

IP 88909D, Anonymous, Mar. 4, 2005.*
The Pesticide Manual, Tomlin, C.D. (Ed.), British Crop Production Council, UK, pp. 34-35 (2009).*

* cited by examiner

*Primary Examiner* — John Pak

(57) ABSTRACT

Herbicidal compositions comprising (a) imazapic or salt thereof, (b) aminopyralid or salt thereof, and optionally (c) metsulfuron or an ester thereof are described herein.

15 Claims, No Drawings

HERBICIDAL COMPOSITIONS CONTAINING IMAZAPIC, AMINOPYRALID AND OPTIONALLY METSULFURON

CROSS REFERENCE TO RELATED APPLICATIONS

This application claims the benefit of U.S. Provisional Patent Application Ser. No. 61/919,046, filed Dec. 20, 2013, the disclosure of which is expressly incorporated herein by reference.

BACKGROUND

The occurrence of undesirable vegetation, e.g., weeds, is a constant problem facing farmers in crops, pastures, and other settings. Weeds compete with crops and negatively impact crop yield. The use of chemical herbicides is an important tool in controlling undesirable vegetation. There remains a need for chemical compositions and weed-control methods that offer a broad spectrum of weed control, selectivity, minimal crop damage, storage stability, ease of handling, higher activity against weeds, and/or a means to address herbicide-tolerance that develops with respect to herbicides currently in use.

SUMMARY

The present disclosure describes compositions comprising the herbicidal active ingredients imazapic or salt thereof and aminopyralid or a salt thereof. In these compositions, the aminopyralid can be aminopyralid triisopropanolammonium salt and the imazapic can be imazapic ammonium salt. The compositions can also include metsulfuron. In these compositions, the imazapic can be imazapic ammonium salt, the aminopyralid can be aminopyralid potassium salt, and the metsulfuron can be metsulfuron-methyl.

Additionally described are methods for controlling undesirable vegetation comprising contacting post-emergently the undesirable vegetation or area adjacent to the vegetation or pre-emergently applying to soil a herbicidally effective amount of the compositions described herein. An example of such a method for controlling undesirable vegetation includes contacting post-emergently the undesirable vegetation or area adjacent to the vegetation or pre-emergently applying to soil a herbicidally effective amount of imazapic or a salt thereof and aminopyralid or a salt thereof, and optionally metsulfuron or an ester thereof.

DETAILED DESCRIPTION

Provided herein are herbicidal compositions comprising the herbicidal active ingredients imazapic or salt thereof and aminopyralid or salt thereof. Also provided herein are herbicidal compositions comprising the herbicidal active ingredients imazapic or salt thereof, aminopyralid or salt thereof, and metsulfuron or ester thereof.

Additionally provided herein are methods of controlling undesirable vegetation comprising applying herbicidally effective amounts of imazapic and aminopyralid or imazapic, aminopyralid, and metsulfuron.

As used herein, imazapic is (±)-2-[4,5-dihydro-4-methyl-4-(1-methylethyl)-5-oxo-1H-imidazol-2-yl]-5-methyl-3-pyridinecarboxylic acid. Imazapic has the following structure:

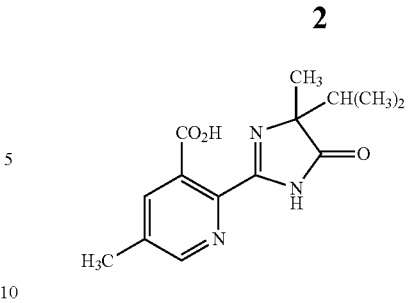

Exemplary herbicidal uses are provided in Tomlin, C. D. S., Ed. *The Pesticide Manual: A World Compendium*, 15th ed.; BCPC: Alton, 2009 (hereafter "*The Pesticide Manual*, Fifteenth Edition, 2009"). Exemplary uses of imazapic include, but are not limited to, the pre- and post-emergent residual control of a wide range of annual and perennial weeds in pasture, rangeland, and non-cropland areas. Exemplary imazapic salts include the ammonium salt.

As used herein, aminopyralid is 4-amino-3,6-dichloro-2-pyridinecarboxylic acid. Aminopyralid has the following structure:

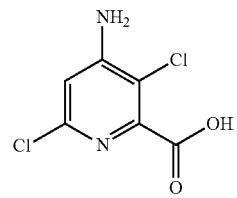 [SMILES: Nc1cc(Cl)nc(C(=O)O)c1Cl]

Exemplary herbicidal uses are described in *The Pesticide Manual*, Fifteenth Edition, 2009. Exemplary uses of aminopyralid include, but are not limited to, its use as a herbicide for the control of annual and perennial grass and broad-leaved weeds in grassland. Exemplary aminopyralid salts include the potassium salt and the triisopropanolammonium salt.

As used herein, metsulfuron is 2-[[[[(4-methoxy-6-methyl-1,3,5-triazin-2-yl)amino]carbonyl]amino]sulfonyl]benzoic acid. Metsulfuron has the following structure:

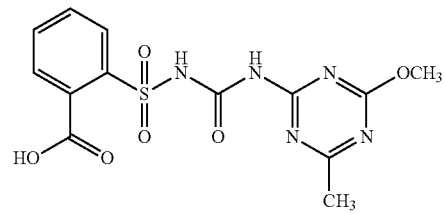

Exemplary herbicidal uses are described in *The Pesticide Manual*, Fifteenth Edition, 2009. Exemplary uses of metsulfuron include, but are not limited to, its use as a post-emergence herbicide for the control of grass and broad-leaved weeds in wheat, barley, rice, oats, and triticale. In certain embodiments, it can be used as the acid itself or as an agriculturally acceptable ester. Exemplary esters include the methyl ester.

As used herein, a herbicidally effective or vegetation controlling amount is an amount of active ingredient (or combination of ingredients) which causes an adversely modifying effect to the vegetation e.g., causing deviations from natural development, killing, effecting regulation, causing desiccation, causing retardation, or the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

In some embodiments, the compositions and methods provided herein are utilized to control weeds in crops, including but not limited to pastures, grasslands, rangelands, fallowland, turf, industrial vegetation mangement (IVM), and rights-of-way.

The compositions and methods described herein can be used to control undesirable vegetation in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant- and bromoxynil-tolerant crops (such as, but not limited to, soybean, cotton, canola/oilseed rape, rice, cereals, corn/maize, turf, etc.), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes-of-action (MOA). In some embodiments, the compositions described herein and other complementary herbicides are applied at the same time, either as a combination formulation, as a tank mix, or as a sequential application.

The compositions and methods provided herein are utilized to control undesirable vegetation. Undesirable vegetation includes, but is not limited to, undesirable vegetation that occurs in pastures, grasslands, rangelands, fallowland, turf, IVM, and rights-of-way.

In some embodiments, the methods provided herein are utilized to control undesirable vegetation found in tree and vine, perennial crops and row crops, including, but not limited to, vineyards, orchards, perennial plantation crops, corn/maize, sorghum, sunflower, canola/oilseed rape and vegetables. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), *Taraxacum officinale* F.H. Wigg (common dandelion, TAROF) or *Xanthium strumarium* L. (common cocklebur, XANST).

In some embodiments, the methods provided herein are utilized to control undesirable vegetation in range and pasture, IVM and rights-of-way. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Melochia parviflora* (escoba blanca, MEOPA), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G.H. Weber ex Wiggers (dandelion, TAROF), *Trifolium repens* L. (white clover, TRFRE), or *Urtica dioica* L. (common nettle, URTDI).

In some embodiments, the compositions and methods provided herein are utilized to control undesirable vegetation consisting of grass, broadleaf and sedge weeds. In certain embodiments, the compositions and methods provided herein are utilized to control members of the genera *Borreria* or *Spermacoce*. In certain embodiments, the compositions and methods provided herein are utilized to control *Borreria*. In some embodiments, the compositions and methods provided herein are utilized to control *Borerria verticillata* (whitehead broom, BOIVE).

Herbicidal activity is exhibited by the compounds when they are applied directly to the plant, to the area adjacent to the plant (i.e., locus) at any stage of growth or before planting or emergence or after emergence. The components of the mixtures described herein can be applied either separately or as part of a multipart herbicidal system.

In some embodiments, the ammonium salt of imazapic is utilized.

In some embodiments, the potassium salt of aminopyralid is utilized. In some embodiments, the triisopropanolammonium salt is utilized.

In some embodiments, the methyl ester of metsulfuron is utilized.

In some embodiments, the aminopyralid herbicide is the potassium salt and the metsulfuron herbicide is the methyl ester of metsulfuron.

In some embodiments, the aminopyralid herbicide is the triisopropanolammonium salt of aminopyralid.

In some embodiments, the composition is a combination of aminopyralid triisopropanolammonium salt and imazapic ammonium salt. In other embodiments, the composition is a combination of imazapic ammonium salt, aminopyralid potassium salt, and metsulfuron-methyl.

In some embodiments, the compositions comprise and methods utilize imazapic and aminopyralid. In some embodiments, the weight ratio (calculated from grams of acid equivalent ("g ac") for components (a) and (b)) of (a) imazapic to (b) aminopyralid is (a) 70-140 to (b) 100. In another embodiment, the weight ratio is (a) 70-140 to (b) 50-200. In another embodiment, the weight ratio is (a) 70-140 to (b) 50-125. In another embodiment, the weight ratio is (a) 70-140 to (b) 87-113. In another embodiment, the weight ratio is (a) 70 to (b) 100. In another embodiment, the weight ratio is (a) 140 to (b) 100.

In some embodiments, the compositions comprise and methods utilize imazapic, aminopyralid and metsulfuron. In some embodiments, the weight ratio (calculated from grams of acid equivalent ("g ae") of components (a) and (b) and grams of active ingredient ("g ai") of component (c)) of (a) imazapic to (b) aminopyralid to (c) metsulfuron is (a) 70-140 to (b) 100 to (c) 18. In another embodiment, the weight ratio is (a) 70-140 to (b) 50-200 to (c) 9-36. In another embodiment, the weight ratio is (a) 70-140 to (b) 50-125 to (c) 9-36. In another embodiment, the weight ratio is (a) 70-140 to (b) 50-125 to (c) 9-45. In another embodiment, the weight ratio is (a) 70-140 to (b) 87-113 to (c) 13.5-22.5. In another embodiment, the weight ratio is (a) 70 to (b) 100 to (c) 18. In another embodiment, the weight ratio is (a) 140 to (b) 100 to (c) 18.

In certain embodiments, imazapic is applied at a rate from about 70 g ae/ha to about 140 g ae/ha, aminopyralid is applied at a rate from about 50 g ae/ha to about 200 g ae/ha, and metsulfuron is applied at a rate from about 9 g ai/ha to 45 g ai/ha. In certain embodiments, imazapic is applied at a rate from about 70 g ae/ha to about 140 g ae/ha, aminopyralid is applied at a rate from about 87 g ae/ha to about 113 g ae/ha, and metsulfuron is applied at a rate from about 13.5 g ai/ha to 22.5 g ai/ha.

The components of the mixtures described herein can be applied either separately, e.g., sequentially, or as a single composition, e.g., premix. In some embodiments, the components are applied within 1, 2, 4, 6, 8, 10, 12, 14, 16, 18, 20, 22, or 24 hours of each other. In some embodiments, the components are applied within 1, 2, 3, 4, 5, 6, or 7 days of each other. In some embodiments, a single application of each component is utilized. In some embodiments, multiple applications of one or more components is utilized.

The mixtures of the present disclosure can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the synergistic composition described herein include, but are not limited to, acid, salt and ester forms of the following herbicides: 4-CPA, 4-CPB, 4-CPP, 2,4-D, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fenquinotrione, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, topramezone, tralkoxydim, triafamone, triallate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compositions of the present disclosure can, further, be used in conjunction with glyphosate, glufosinate, dicamba, imidazolinones, sulfonylureas, ACCase inhibitors (aryloxyphenoxyproprionates and cyclohexanediones) or 2,4-D on glyphosate-tolerant, glufosinate-tolerant, dicamba-tolerant, imidazolinone-tolerant, sulfonylurea-tolerant, ACCase inhibitor-tolerant and 2,4-D-tolerant crops. In some embodiments, the compositions described herein are used in combination with herbicides that are selective for the crop being treated and which complement the spectrum of weeds controlled by these compounds at the application rate employed. In other embodiments, the compositions of the present disclosure and other complementary herbicides are applied at the same time, either as a combination formulation or as a tank-mix.

The compositions of the present disclosure can be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

In practice, the compositions described herein are used in mixtures containing a herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or an area adjacent to the weed or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions.

Suitable agricultural adjuvants and carriers that are useful in preparing the herbicidal mixtures described herein are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In some embodiments, water is used for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, it is desirable to incorporate one or more surface-active agents into the compositions of the present disclosure. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998 and in *Encyclopedia of Surfactants, Vol. I-III*, Chemical Publishing Co., New York, 1980-81. Typical surface-active agents include salts of alkyl sulfates, such as diethanolammonium lauryl sulfate; alkylarylsulfonate salts, such as calcium dodecylbenzene-sulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the synergistic composition of the present disclosure is from 0.1 to 98 percent by weight, and in other embodiments, concentrations from 10 to 90 percent by weight are employed. In certain embodiments in which the compositions are designed to be employed as concentrates, the active ingredients may be present in a concentration from about 5 to about 98 weight percent, and in other embodiments from about 10 to about 90 weight percent. Such compositions may be diluted with an inert carrier, such as water, before making a post-emergence, foliar application to exposed weed and crop foliage, or may be applied as a dry or liquid formulation directly into flooded rice fields or other aquatic conditions. In some embodiments the diluted compositions are applied as a post-emergence, foliar application to weeds or the area adjacent to the weeds and contain from about 0.02 to about 20 weight percent active ingredient and in other embodiments contain from about 0.04 to about 10 weight percent active ingredient.

The present compositions can be applied to weeds or the area adjacent to the weeds by the use of conventional ground or aerial dusters, sprayers, and granule applicators, by addition to irrigation or paddy water, and by other conventional means known to those skilled in the art.

The following Examples are presented to illustrate various aspects of the compositions and methods described herein and should not be construed as limitations to the claims.

EXAMPLES

Evaluation of Postemergence Herbicidal Activity of Mixtures in the Field

Field trials were conducted in Brazil in pasture area cultivated with *Brachiaria brizantha* using standard herbicide small-plot research methodology. The plot size used was 3×8 meter (m; width×length) with 4 replicates per treatment. The pasture was grown using normal cultural practices for fertilization, management, and maintenance to ensure good growth of the crop and the weeds.

All treatments in the field trials were applied using a carbon dioxide ($CO_2$) backpack air sprayer with flat fan nozzles (110.03°), calibrated to apply 250 liters per hectare (L/ha) spray volume at approximately 35 pounds per square inch (PSI). Formulations of aminopyralid (triisopropanolammonium salt) at 100 grams acid equivalent per hectare (g ae/ha) and aminopyralid (potassium salt, 525grams acid equivalent per kilogram (g ae/kg))+metsulfuron-methyl (94.5 grams active ingredient per kilogram (g ai/kg)) at 118 grams per hectare (g/ha) were mixed with imazapic at 70 and 140 g ae/ha and water+Joint Mineral Oil at appropriate formulated product rates to achieve the desired rates based on a unit area of application (hectare) as shown. Treatments were rated at 15 to 281 days after application (DAA) as compared to the untreated control plants. Visual weed control of BOIVE was scored on a scale of 0 to 100 percent where 0 corresponds to no injury and 100 corresponds to complete kill.

Tables 1 and 2 demonstrate the herbicidal synergistic efficacy on weed control of three herbicidal active ingredients, imazapic, aminopyralid and metsulfuron. All treatment results, both for the single product and mixtures, are an average of 3 to 4 replicates and the tank-mix interactions are significant at the P>0.05 level.

Colby's equation was used to determine the herbicidal effects expected from the mixtures (Colby, S.R. Calculation of the synergistic and antagonistic response of herbicide combinations. *Weeds* 1967, 15, 20-22).

The following equation was used to calculate the expected activity in Table 1 for mixtures containing two active ingredients, A and B:

Expected=$A+B-(AB/100)$

A=observed efficacy of active ingredient A (Imazapic) at the same concentration as used in the mixture;

B=observed efficacy of active ingredient B (Aminopyralid) at the same concentration as used in the mixture.

The experiments described herein in Table 2 were performed such that the "B" component in Colby's equation was the activity for the combination of aminopyralid and metsulfuron and only the activity for the combination was determined. As such, Colby's equation could be written as Expected=$A+Z-(AZ/100)$ A=observed efficacy of active ingredient A (Imazapic) at the same concentration as used in the mixture;

Z=observed efficacy of aminopyralid combined with metsulfuron at a constant concentration.

Some of the compounds tested, application rates employed, plant species tested, and results are given in Tables 1 and 2. All comparisons are an average of 3 to 4 replicates and are significant at the P>0.05 level.

TABLE 1

Synergistic weed control of BOIVE using Imazapic + Aminopyralid

| Imazapic* | Aminopyralid** | % Visual Control BOIVE (281 DAA) | |
|---|---|---|---|
| g ae/ha | g ae/ha | Obs | Exp |
| 70 | 0 | 0 | — |
| 140 | 0 | 14 | — |
| 70 | 100 | 56 | 41 |
| 140 | 100 | 65 | 49 |
| 0 | 100 | 41 | — |

*ammonium salt
**triisopropanolammonium salt

TABLE 2

Synergistic weed control of BOIVE using Imazapic + Aminopyralid + Metsulfuron

| Imazapic* | Aminopyralid** | Metsulfuron*** | % Visual Control BOIVE (281 DAA) | |
|---|---|---|---|---|
| g ae/ha | g ae/ha | g ai/ha | Obs | Exp |
| 70 | 0 | 0 | 0 | — |
| 140 | 0 | 0 | 14 | — |
| 70 | 100 | 18 | 78 | 36 |
| 140 | 100 | 18 | 84 | 45 |
| 0 | 100 | 18 | 36 | — |

*ammonium salt
**potassium salt
***methyl ester

BOIVE: whitehead broom (*Borerria verticillata*)
g ae/ha: grams acid equivalent per hectare
g ai/ha: grams active ingredient per hectare The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term comprising and variations thereof as used herein is used synonymously with the term including and variations thereof and are open, non-limiting terms.

What is claimed is:

1. A herbicidal composition comprising the herbicidal active ingredients imazapic or salt thereof, aminopyralid or a salt thereof, and metsulfuron or ester thereof, wherein the weight ratio with respect to grams of imazapic or salt thereof to grams of aminopyralid or salt thereof to grams of metsulfuron or ester thereof is 70-140:100:18.

2. The composition of claim 1, wherein the aminopyralid herbicidal active ingredient is aminopyralid triisopropanolammonium salt.

3. The composition of claim 1, wherein the imazapic herbicidal active ingredient is imazapic ammonium salt.

4. The composition of claim 1, wherein the aminopyralid herbicidal active ingredient is aminopyralid potassium salt.

5. The composition of claim 1, wherein the metsulfuron herbicidal active ingredient is metsulfuron-methyl.

6. The composition of claim 1, further comprising a herbicidally acceptable adjuvant or carrier.

7. A method for controlling undesirable vegetation comprising contacting post-emergently the undesirable vegetation or area adjacent to the vegetation or pre-emergently applying to soil a herbicidally effective amount of the composition of claim 1.

8. A method for controlling undesirable vegetation comprising contacting post-emergently the undesirable vegetation or area adjacent to the vegetation or pre-emergently applying to soil a herbicidally effective amount of imazapic or a salt thereof, aminopyralid or a salt thereof, and metsulfuron or an ester thereof, wherein the weight ratio with respect to grams of imazapic or salt thereof to grams of aminopyralid or salt thereof to grams of metsulfuron or ester thereof is 70-140:100:18.

9. The method of claim 8, wherein the method is performed post-emergently in a pasture.

10. The method of claim 8, wherein the undesirable vegetation is *Borreria* or *Spermacoce*.

11. The method of claim 8, wherein the undesirable vegetation is *Borreria verticillata*.

12. The method of claim 8, wherein the imazapic herbicidal active ingredient is imazapic ammonium salt.

13. The method of claim 8, wherein the aminopyralid herbicidal active ingredient is aminopyralid potassium salt.

14. The method of claim 8, wherein the metsulfuron herbicidal active ingredient is metsulfuron-methyl.

15. The method of claim 8, wherein the aminopyralid herbicidal active ingredient is aminopyralid triisopropanolammonium salt.

* * * * *